United States Patent [19]
Moreland

[11] Patent Number: 5,824,047
[45] Date of Patent: *Oct. 20, 1998

[54] VASCULAR GRAFT FABRIC

[75] Inventor: Janet L. Moreland, Newburyport, Mass.

[73] Assignee: C. R. Bard, Inc., Murray Hill, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 728,750

[22] Filed: Oct. 11, 1996

[51] Int. Cl.⁶ .................................................. A61F 2/06
[52] U.S. Cl. .................................. 623/1; 623/12; 623/66; 600/36
[58] Field of Search ............................ 623/1, 11, 12, 623/66; 600/36

[56] References Cited

U.S. PATENT DOCUMENTS

| | | |
|---|---|---|
| 2,978,787 | 4/1961 | Liebig . |
| 2,990,605 | 7/1961 | Demsyk . |
| 3,001,262 | 9/1961 | Parker . |
| 3,096,560 | 7/1963 | Liebig . |
| 3,304,557 | 2/1967 | Polansky ............................. 623/1 |
| 3,316,557 | 5/1967 | Liebig . |
| 4,155,394 | 5/1979 | Sheperd et al. . |
| 4,164,045 | 8/1979 | Bokros et al. . |
| 4,191,218 | 3/1980 | Clark et al. . |
| 4,323,525 | 4/1982 | Bornat . |
| 4,340,091 | 7/1982 | Skelton et al. . |
| 4,441,215 | 4/1984 | Kaster . |
| 4,517,687 | 5/1985 | Liebig et al. . |
| 4,530,113 | 7/1985 | Matterson . |
| 4,610,688 | 9/1986 | Silvestrini et al. . |
| 4,634,625 | 1/1987 | Franklin . |
| 4,652,263 | 3/1987 | Herweck et al. ............................. 623/1 |
| 4,670,286 | 6/1987 | Nyilas et al. . |
| 4,816,028 | 3/1989 | Kapadia et al. . |
| 4,892,539 | 1/1990 | Koch . |
| 4,965,110 | 10/1990 | Berry . |
| 4,969,896 | 11/1990 | Shors . |
| 4,987,665 | 1/1991 | Dumican et al. . |
| 4,990,158 | 2/1991 | Kaplan et al. . |
| 5,084,065 | 1/1992 | Weldon et al. . |
| 5,116,360 | 5/1992 | Pinchuk et al. . |
| 5,127,919 | 7/1992 | Ibrahim et al. . |
| 5,178,630 | 1/1993 | Schmitt . |
| 5,217,495 | 6/1993 | Kaplan et al. . |
| 5,244,718 | 9/1993 | Taylor et al. . |
| 5,275,622 | 1/1994 | Lazarus et al. . |
| 5,282,846 | 2/1994 | Schmitt . |
| 5,282,847 | 2/1994 | Trescony et al. . |
| 5,282,848 | 2/1994 | Schmitt . |
| 5,413,598 | 5/1995 | Moreland ................................. 623/12 |
| 5,476,507 | 12/1995 | Wakabayashi et al. ..................... 623/1 |
| 5,562,725 | 10/1996 | Schmitt et al. ............................ 623/12 |
| 5,569,273 | 10/1996 | Titone et al. .............................. 623/11 |
| 5,611,127 | 3/1997 | Ceriani et al. ............................... 623/1 |

FOREIGN PATENT DOCUMENTS

| | | |
|---|---|---|
| 0 108 171 A1 | 5/1984 | European Pat. Off. . |
| 0 122 744 A1 | 10/1984 | European Pat. Off. . |
| 0 128 741 A1 | 12/1984 | European Pat. Off. . |
| 0 246 638 A2 | 11/1987 | European Pat. Off. . |
| 0 308 102 A1 | 3/1989 | European Pat. Off. . |
| 0 327 903 A2 | 8/1989 | European Pat. Off. . |
| 0 461 791 A1 | 12/1991 | European Pat. Off. . |
| 0464755 | 1/1992 | European Pat. Off. ................. 623/12 |
| 0 501 890 A1 | 9/1992 | European Pat. Off. . |
| 0 002 931 A1 | 7/1979 | United Kingdom . |
| 2 120 946 | 12/1983 | United Kingdom . |
| WO 87/05796 | 10/1987 | WIPO . |
| WO 89/08433 | 9/1989 | WIPO . |
| WO 92/03107 | 3/1992 | WIPO . |
| WO 94/15548 | 7/1994 | WIPO . |
| WO 94/24960 | 11/1994 | WIPO . |

*Primary Examiner*—Michael J. Milano
*Assistant Examiner*—Tram Anh T. Nguyen
*Attorney, Agent, or Firm*—Wolf, Greenfield & Sacks, P.C.

[57] ABSTRACT

A woven vascular graft fabric that permits limited radial compliance but resists long term dilation and longitudinal extension. The thin walled graft has a double wall thickness of less than 0.02 inches and a greater number of picks per inch than ends per inch.

14 Claims, No Drawings

VASCULAR GRAFT FABRIC

FIELD OF INVENTION

This invention relates to a vascular graft fabric and, more particularly, to a vascular graft fabric for use in the repair of an abdominal aortic aneurysm.

BACKGROUND OF THE INVENTION

Various synthetic vascular grafts have been proposed to replace, bypass or reinforce, diseased or damaged sections of a vein or artery. Such tubular grafts commonly are formed either by knitting, weaving or braiding continuous filament polyester fiber or by expanding polytetraflouroethylene (PTFE).

Synthetic grafts have been indicated specifically for the repair of an abdominal aortic aneurysm, which is presented by a weakened wall of the aorta between the renal arteries and the bifurcation to the iliac arteries. Rupture of an aneurysm may cause massive internal bleeding, posing a life threatening risk to the patient. Current treatment involves implanting a graft between the infra renal and distal aorta so that the prosthetic spans the weakened region. The graft conduit mitigates the pressure felt by the aneurysm limiting further dilation of the compromised arterial wall. The vascular graft may be placed either invasively, through abdominal surgery, or non-invasively, through percutaneous endoluminal transport.

Percutaneous delivery of a graft avoids the complications and risk of abdominal surgery. Current knitted and woven vascular grafts for repairing abdominal aortic aneurysms have a wall thickness of at least 0.02 inches. An introducer sheath of at least 22 French is required to deliver such prosthetics endoluminally, excluding the use of the femoral artery as an access site for a certain class of patients. It would be beneficial to provide a thinner graft that is percutaneously deliverable through the vasculature of the previously excluded class of patients. A graft with a reduced wall thickness also should be easier to traverse through the tortuous iliac arteries leading to the weakened aortic section.

Knitted prosthetics, however, are particularly susceptible to radial dilation where the high pressure aortic blood flow expands the knitted prosthetic outwardly against the thin and distended aortic wall, potentially leading to rupture of the aneurysm. It is not uncommon for conventional knitted grafts to dilate 50 to 100% at the physiologic pressures of interest (120–200 mm Hg). Reducing the wall thickness would be expected to exacerbate this problem. Knitted grafts also are susceptible to longitudinal expansion which can result in unintended occlusion of an artery, such as an iliac artery when the prosthetic is used in the repair of an abdominal aortic aneurysm. Although long term radial dilation of knitted grafts is detrimental, it may be advantageous to have limited, radial expansion which conforms the ends of the graft to the dimensions of the healthy sections of arterial wall surrounding the defect. Such a compliant knitted graft is unlikely to leave gaps between the prosthetic and the anchoring segments of the aortic wall that otherwise could present significant health risk to the patient. For conventional placement, compliance facilitates sewing of an anastomosis.

Conventional woven grafts, on the other hand, are relatively inextensible and therefore generally do not present the radial or longitudinal dilation concerns posed by knitted grafts. Because they are not radially compliant, however, woven grafts require precise sizing of the aorta to ensure that a suitably dimensioned prosthetic is selected for implantation. This characteristic is particularly inconvenient for percutaneous applications. Representative of a woven vascular prosthetic is the Soft Woven graft available from Bard Vascular Systems Division of C. R. Bard, Inc., assignee of the present application. The Soft Woven graft is formed in a plain weave from dual ply, 70 denier and 47 filament polyester yarn. The Soft Woven graft has a double wall thickness of 0.022" and a thread count of 125 ends/inch and 72 picks/inch. The Soft Woven graft is not radially compliant (less than 5 percent at physiologic pressure) and exhibits negligible, if any, long term dilation or longitudinal extension.

Consequently, it would be desirable to provide a thin walled synthetic vascular graft that combines the favorable attributes of woven and knitted grafts, providing radial compliance while resisting long term dilation and longitudinal extension.

SUMMARY OF THE INVENTION

The present invention is a biologically implantable, woven vascular graft fabric for augmenting or replacing a damaged or weakened vessel segment. The graft fabric may be woven into a seamless tube or, alternatively, a woven fabric sheet may be formed into a cylindrical configuration and sewn along a seam to provide the desired tubular shape. Single and multiple lumen grafts (e.g., bifurcated, trifurcated, etc.) are contemplated. The prosthetic is provided with sufficient dimensions to bridge the damaged region of the vessel, with the proximal and distal ends seating in healthy regions surrounding the defect. When used in the repair of an abdominal aortic aneurysm, the vascular graft shields the compromised arterial wall from pressure associated with normal pulsatile flow, eliminating continued aneurysm growth and preventing rupture of the thin, distended wall segment.

The thin vascular graft fabric has a double wall thickness of preferably less than 0.020 inches. The fine fabric is collapsible into a slender shape which facilitates percutaneous transport and allows the employment of small delivery instruments that are accessible through the femoral vasculature. The prosthetic allows limited radial compliance so that the ends of the graft may register against the healthy sections of the vessel surrounding the defect, minimizing the formation of gaps between the implant and the vessel wall being augmented. Compliance of the graft to the vessel wall enhances tissue ingrowth and provides a smooth transition for blood flow from the healthy portion of the vessel into the graft. Fluoroscopic imaging and an angiogram may be performed to verify implant position and to assess graft patency. Resilient anchors and struts may be employed in the percutaneously deliverable graft and will encourage compliance when the compressed framework expands upon deployment at the repair site. Long term radial dilation of the graft is prevented, reducing the likelihood of rupture of the aneurysm due to outward expansion of the prosthetic against the weakened vessel wall. The graft exhibits negligible longitudinal stretch, minimizing the incidence of occlusion of the iliac artery by in vivo stretch or creep of the graft into or across the aortic bifurcation, when employed in the repair of an abdominal aortic aneurysm.

In one embodiment of the invention, the vascular graft fabric is woven from texturized, biologically compatible fibers in a plain weave with a greater number of picks per inch than ends per inch, preferably in a ratio of greater than 1.0 to 1.8 and, more preferably, a ratio of about 1.6. The percutaneously deliverable tubular fabric has a wall thickness (double wall) of less than 0.02 inches and preferably of about 0.01 inches. The graft fabric exhibits limited radial compliance in excess of 5 percent and, preferably, in excess of 10 percent but that does not exceed 35 percent of the graft outer diameter when fluid flows through the graft at physiologic pressure (120 mm–200 mm Hg). A preferred range of radial compliance is 10 to 35 percent and a more preferred range is from 10 to 25 percent. Long term fluid flow (approximately 72 hours) through the graft at physiological pressure does not reveal that radial dilation (defined as more than 5 percent additional radial expansion) or appreciable longitudinal extension has occurred.

It is among the general objects of the invention to provide a thin walled vascular graft fabric which is radially compliant but is resistant to long term dilation and longitudinal extension.

It is another object of the invention to provide a thin walled vascular graft fabric that may be deployed percutaneously through an 18 Fr delivery system.

It is a still further object of the invention to provide a vascular graft fabric for treating a vascular aneurysm, such as an aortic aneurysm.

Other objects and features of the present invention will become apparent from the following detailed description which discloses multiple embodiments of the invention. It is to be understood that the specification is intended to explain one or more embodiments of the invention but is not a definition of the limits of the invention.

DESCRIPTION OF PREFERRED EMBODIMENT

A preferred embodiment of the vascular graft fabric, particularly indicated for use in the repair of an abdominal aortic aneurysm, is formed from single ply, 50 denier, 47 filament (1/50/47) pretexturized, high shrinkage (in excess of approximately 15%), polyethylene terephthalate (PET) yarns woven in a plain weave pattern with 83 ends/inch and 132 picks/inch (prior to processing). The vascular graft fabric, prior to processing, has a double wall size of less than 0.02 inches and preferably has a double wall thickness of about 0.01 inches. Although polyester yarns are preferred, other biologically compatible synthetic fibers can be used, including nylon and polypropylene. The yarns may be twisted prior to weaving and a graft with 8 twists per inch has provided acceptable properties. Other weave patterns, yarn sizes (including microdenier) and thread counts also are contemplated so long as the resulting fabric has the desired thinness, radial compliance and resistance to long term radial dilation and longitudinal expansion.

The woven fabric is washed at an appropriate temperature, such as between 60°–90° C., and then is steam set over a mandrel to provide the desired tubular configuration. The graft is then dried in an oven or in a conventional dryer at approximately 150° F. Any of the washing, steaming and drying temperatures may be adjusted to affect the amount of shrinkage of the fabric yarns. It is believed that shrinkage causes the small, tightly bundled weft yarns to loop above and below adjacent warp yarns. The resulting slack in the weft yarns allows the graft to stretch radially in response to the pressurized blood flow until the undulations in the weft yarns straighten out at which time the non-elastic yarns will resist further outward expansion. In this manner, the prosthetic is radially compliant to the extent necessary for the ends of the graft to conform to the slightly larger anchoring sections of the aorta, but resists radial dilation that otherwise could lead to rupture of the aneurysm and axial extension that could block the entrance to an iliac artery.

Radial dilation is considered to occur when a graft expands a further 5% after radial compliance. The 5% window allows for slight radial expansion due to the inherent stretch in the yarn of the fabric.

The thin walled, woven vascular graft fabric may be formed into a tubular configuration and collapsed into a reduced profile for percutaneous delivery of the prosthetic to the delivery site. The implant is sufficiently resilient so that it will revert back to its normal, expanded shape upon deployment either naturally or under the influence of resilient anchors that secure the implant to the vessel wall, and or, alternatively, struts that prevent compression and twisting of the implant. The thin wall structure allows small delivery instruments (18 Fr or smaller) to be employed when the graft is percutaneously placed. The fine wall thickness also is believed to facilitate the healing process. The graft, when used for the repair of an abdominal aortic aneurysm, may be provided in a variety of outer diameters and lengths to match the normal range of aortic dimensions. It is contemplated to provide the prosthetic in outer diameters ranging from 14 to 24 mm, in 2 mm increments, and of lengths ranging from 8 to 14 cm, in 1 cm increments. Of course, other dimensions and increments would be appropriate for the repair or replacement of other types of vasculature.

The biologically compatible prosthetic fabric encourages tissue ingrowth and the formation of a neointima lining along the interior surface of the graft, preventing clotting of blood within the lumen of the prosthetic which could occlude the graft. The graft has sufficient strength to maintain the patency of the vessel lumen and sufficient burst resistance to conduct blood flow at the pressures encountered in the aorta without rupturing. The graft may be preclotted with either the patient's own blood or by coating the fabric with an impervious material such as albumin, collagen or gelatin to prevent hemorrhaging as blood initially flows through the graft. Although a constant diameter graft is preferred, a varying dimensioned prosthetic also is contemplated. The graft may be provided with one or more radiopaque stripes to facilitate fluoroscopic or X-ray observation of the graft.

The vascular graft fabric will now be described in connection with the non-invasive, percutaneous repair of an abdominal aortic aneurysm. The woven prosthetic is provided with a non-ferrous, self expanding wire anchor at each end. The renal or proximal anchor has hooks to prevent migration of the graft while the iliac or distal anchor is hookless. Longitudinal struts may extend between the renal and iliac anchors to prevent compression and twisting of the implant. Pre-treatment diagnostic procedures are employed to verify that the non-dilated aortic wall proximal and distal of the aneurysm is capable of accepting the anchoring mechanisms for provisionally securing the implant until there is sufficient tissue ingrowth.

Anterior and posterior imaging of the aorta is employed to determine the proper implant length. An ultrasound catheter is used to measure cross-sectional area and diameter of the compromised wall section. An average diameter of the infrarenal aorta is used to select the appropriate implant size. An implant of desired diameter and length is removed from its sterile packaging and is contracted and loaded into an 18 Fr (6 mm) introducer sheath. The delivery system is inserted through a cut down in the femoral artery and is advanced to the damaged region over a previously emplaced guidewire. When proper positioning of the implant is confirmed, the endoprosthesis is ejected and the renal and iliac anchors expand and engage the non-dilated aorta wall, reducing the risk of the graft assembly migrating from its deployed location. The resilient action of the anchors, together with the force of the pulsatile blood flow, outwardly spreads and expands the wall of the graft into compliance with the luminal surface of the aorta.

In order to further illustrate the invention, the following example is provided reciting certain average or approximate properties of the thin walled vascular graft and the commercially available Soft Woven graft. It is to be understood, however, that the example is included for illustrative purposes only and is not intended to limit the scope of the invention as set forth in the accompanying claims.

EXAMPLE

Normalized radial tensile analysis (strength) was conducted on an Instron 4202 arranged with radial tensile jaws and a 200 lb load cell. Crosshead speed was ten inches per minute with proportions of 1:1. Half inch long samples were mounted in the jaws of the Instron and were pulled until failure. Several samples were tested providing an average tensile strength.

Permeability represents the amount of water that flows through a square centimeter of fabric in one minute at a pressure of 120 mm Hg. Flat fabric samples were mounted about a testing orifice and then were prewetted to minimize the effect of entrapped air or microbubbles attached to the material surface. The test was conducted pursuant to the American National Standard for Vascular Graft Prostheses 4.3.1.2(1)(b).

Burst resistance is the amount of pressure a fabric can withstand without rupturing. A tubular graft is lined with a highly compliant non-permeable membrane, such as a balloon or condom, to prevent air from escaping. The ends of the graft as clamped to adapters with one end being connected to a source of pressurized gas. The pressure is gradually increased until the fabric ruptures with burst strength being the pressure at rupture.

Compliance is the change in diameter as a function of the change in pressure. The graft is again lined with a non-permeable membrane which is inflated to a pressure of 200 mmHg. The diameter is measured using a laser microscope with compliance being calculated as the diameter at 200 mmHg—diameter at 0 pressure/diameter at 0 pressure.

Longitudinal extension is the change in length at a pressure of 200 mmHg and can be measured using the same setup as in the compliance test. The closed end of the fabric is mounted onto a sliding track with a calibrated ruler at the bottom. Less than 5% extension is considered to be non-appreciable.

Dilation is the change in diameter over time (72 hours) at physiological pressure. A balloon lined fabric is placed in the same fixture used for compliance measurements and is inflated to 200 mmHg. Diameter measurements are taken with a laser microscope every few hours. Long term dilation is calculated by the final diameter at 200 mmHg—initial diameter at 200 mmHg/initial diameter at 200 mmHg.

| Property | Soft Woven | Thin Wall |
| --- | --- | --- |
| Yarns | 2/70/47 | 1/50/47 |
| Fabric Construction (pre-processing) | plain weave | plain weave |
| | 125 ends/inch | 83 ends/inch |
| | 72 picks/inch | 132 picks/inch |
| Double Wall Thickness (pre-processing) | .022" | .010" |
| Radial Tensile Strength | >70 lbs | ~60 lbs |
| Burst Strength | ~200 psi | ~40 psi |
| Water Permeability | 131 cc/cm²/min | 2350 cc/cm²/min |
| Compliance | <5% | 24% at 120–200 mmHg |
| Long Term Dilation | none (estimated) | none (<5%) |

It should be understood that the foregoing description of the invention is intended merely to be illustrative thereof and that other embodiments, modifications, and equivalents of the invention may be within the scope of the invention recited in the claims appended hereto.

I claim:

1. A vascular graft fabric for repairing or augmenting a weakened vascular wall, comprising:

a biologically compatible and implantable weave of synthetic yarns having a greater number of picks per inch than ends per inch and having a double wall thickness of less than 0.02 inches, wherein said weave is formable into a tubular configuration having an outer diameter and a lumen extending therethrough which exhibits limited radial compliance, greater than 5 percent but that does not exceed 35 percent of the outer diameter when a fluid at a physiologic pressure of 120–200 mm Hg is flowing through the lumen and wherein the tubularly configured weave does not exhibit radial dilation, more than an additional 5% beyond the limited radial compliance, or appreciable longitudinal expansion after flow of fluid through the lumen at a physiologic pressure of 120–200 mm Hg for approximately 72 hours.

2. The vascular graft fabric recited in claim 1 wherein said limited radial compliance is between 10 and 35 percent of the outer diameter of the tubularly configured weave.

3. The vascular graft fabric recited in claim 1 wherein said limited radial compliance is between 15 and 25 percent of the outer diameter of the tubularly configured weave.

4. The vascular graft fabric recited in claim 1 wherein said weave is a plain weave.

5. The vascular graft fabric recited in claim 1 wherein said weave is constructed and arranged in a tubular configuration and has a lumen for conveying blood therethrough.

6. The vascular graft fabric recited in claim 1 wherein said weave is constructed and arranged as a sheet.

7. The vascular graft fabric recited in claim 5 wherein said tubular configuration has a uniform diameter.

8. The vascular graft fabric recited in claim 5 wherein said tubular configuration includes at least one bifurcation.

9. The vascular graft fabric recited in claim 5 wherein said tubular configuration has an outer diameter ranging from 14 to 24 mm.

10. The vascular graft fabric recited in claim 1 wherein the ratio of picks per inch to ends per inch ranges from greater than 1 to 1.8.

11. The vascular graft fabric recited in claim 1 wherein said weave has a double wall thickness of about 0.01 inches.

12. The vascular graft fabric recited in claim 5 wherein said tubular configuration is collapsible into a slender configuration that is percutaneously deliverable through an 18 French introducer.

13. The vascular graft fabric recited in claim 10 wherein said ratio is about 1.6.

14. The vascular graft fabric recited in claim 1, wherein the biologically compatible and implantable weave of synthetic yarns includes a single ply weave.

* * * * *